United States Patent [19]
Lamborne et al.

[11] Patent Number: 6,073,759
[45] Date of Patent: Jun. 13, 2000

[54] PRE-FILLED PACKAGE CONTAINING UNIT DOSE OF MEDICAL GAS AND METHOD OF MAKING SAME

[75] Inventors: Andrew N. Lamborne, Denver, Colo.; Eugene de Juan, Jr., Phoenix, Md.

[73] Assignee: Johns Hopkins University, Baltimore, Md.

[21] Appl. No.: 09/252,682

[22] Filed: Feb. 22, 1999

Related U.S. Application Data

[63] Continuation-in-part of application No. 08/838,824, Apr. 10, 1997, abandoned.

[51] Int. Cl.[7] .......................... B65D 81/20; A61M 31/00
[52] U.S. Cl. ..................... 206/213.1; 206/365; 604/26; 604/521
[58] Field of Search ................... 206/213.1, 364–366, 206/438, 571; 604/23, 25, 26, 521

[56] References Cited

U.S. PATENT DOCUMENTS

| | | | |
|---|---|---|---|
| 3,112,747 | 12/1963 | Cowley | 206/365 |
| 3,494,726 | 2/1970 | Barasch | 21/58 |
| 3,937,219 | 2/1976 | Karakashkian | 128/184 |
| 4,055,672 | 10/1977 | Hirsch et al. | 426/127 |
| 4,135,622 | 1/1979 | Glick | 206/63.3 |
| 4,236,633 | 12/1980 | Ernerst | 206/213.1 |
| 4,449,632 | 5/1984 | Marusiakh, Jr. | 206/540 |
| 4,537,305 | 8/1985 | Takanashi | 206/438 |
| 4,664,256 | 5/1987 | Halskov | 206/213.1 |
| 4,878,903 | 11/1989 | Mueller | 604/199 |
| 5,014,494 | 5/1991 | George | 53/425 |
| 5,037,384 | 8/1991 | Chang | 604/28 |
| 5,234,105 | 8/1993 | Sato et al. | 206/330 |
| 5,256,154 | 10/1993 | Liebert et al. | 604/199 |
| 5,336,175 | 8/1994 | Mames | 604/49 |
| 5,377,835 | 1/1995 | Cornelissen et al. | 206/455 |
| 5,390,792 | 2/1995 | VanNess et al. | 206/439 |

*Primary Examiner*—Jim Foster
*Attorney, Agent, or Firm*—Peter F. Corless; Dike, Bronstein, Roberts & Cushman, LLP

[57] ABSTRACT

A unit dose, gas-filled syringe is provided which is filled with gas and packaged in a gas barrier material prior to use to increase shelf-life, that is, to minimize gas leakage and dilution of the contents of the syringe. The syringe is filled with a selected gas and sealed inside a container made from a high gas barrier material. The container is also filled with the selected gas. The container material is selected to have a gas transmission rate sufficient to prevent the selected gas from diffusing out of the container into the atmosphere. The volume of gas in the container is greater that atmospheric pressure to prevent atmospheric contaminants from entering the container and syringe.

22 Claims, 4 Drawing Sheets

FIG. 2

PRE-FILLED PACKAGE CONTAINING UNIT DOSE OF MEDICAL GAS AND METHOD OF MAKING SAME

CROSS-REFERENCE TO RELATED APPLICATION

This application is a continuation-in-part application of Ser. No. 08/838,824, filed Apr. 10, 1997, abandoned, which is hereby incorporated by reference in its entirety.

FIELD OF THE INVENTION

The invention relates generally to a pre-filled package containing a unit dose of medical gas and a method of making same. The invention is further directed to a method of introducing a unit dose for a gas into a patient using the prefilled syringe.

BACKGROUND OF THE INVENTION

Gas-filled syringes are useful for a number of applications such as surgical procedures involving the injection of a gas bubble into a patient's body. For example, a retinal tear can be treated using an intraocular surgical procedure during which a gas such as sulfur hexafluoride ($SF_6$) or perfluoropropane ($C_3F_8$) is injected into the eye for gas tamponage. Carbon dioxide ($CO_2$) gas can be injected into a blood vessel to facilitate percutaneous angioscopy. Nitric oxide (NO) gas and NO-releasing compounds can also be used to treat a number of medical conditions. For example, NO and NO-releasing compounds can be used for treatment of male impotence, inhibition of DNA synthesis and mitochondrial respiration in tumor cells, and relaxation of vascular smooth muscle for control of hypertension.

Gases used for surgery are often expensive and not available for purchase in ready-to-use form. Currently, gases for surgical procedures are purchased in a pressurized tank. Syringes are filled directly from the tank using a filling line. When a syringe is disconnected from the filling line, the gas in the filling line is released into the atmosphere. Thus, this method of preparing syringes for surgery is disadvantageous because a significant amount of gas is wasted. Due to the busy environment of a hospital, shut-off valves on gas tanks are frequently left open accidentally, causing an even greater amount of gas to be wasted than when gas syringes are being filled.

In addition to the problem of wasting expensive gases, a more serious clinical problem associated with filling syringes from gas tanks is dilution of the gas in the syringe prior to surgery. Syringes are sometimes prepared on the morning of the day they are to be used in surgery. The syringes are then placed in the operating room with other surgical devices until they are needed, which can be several hours later. Experiments have shown that leakage of gas from a syringe over a relatively short period of time can cause clinically significant dilution of the gas dose and therefore increase the risk of surgical complications. For instance, the concentration of sulfur hexafluoride in a plastic syringe has been observed to decrease from 97% at 30 seconds after aspiration to 76% at 60 minutes and 2% at 18 hours past aspiration.

SUMMARY OF THE INVENTION

The present invention overcomes the above-described disadvantages associated with known methods for preparing gas-filled syringes, while also realizing a number of advantages. In accordance with one aspect of the invention, a unit dose, gas-filled syringe is provided which is filled with gas and packaged in a gas barrier material prior to use to increase shelf-life, that is, minimize gas leakage and dilution of the contents of the syringe. The syringe is initially filled with a selected gas and sealed inside a container made from a high gas barrier material. The container is then also filled with the selected gas. The container material is selected to have a gas transmission rate sufficient to prevent the selected gas from diffusing out of the container into the atmosphere and to prevent atmospheric gas contaminants from entering the container. The gas is a pharmaceutically acceptable gas for injecting into the body of an animal. The gas is substantially free of oxygen and air and is at least 70% pure, and preferably 97% pure by volume.

In accordance with another aspect of the present invention, a method of packaging a gas-filled syringe is provided which comprises the steps of forming a container from a gas barrier material to enclose the syringe, placing the gas-filled syringe in the container, filling the container with the same gas as in the pre-filled gas syringe, and sealing the container to retain the gas and the syringe therein.

In accordance with yet another aspect of the present invention, a method of packaging a gas-filled syringe is provided which comprises the steps of forming a container from a gas barrier material to enclose the syringe, the container comprising a valve, placing the gas-filled syringe in the container, sealing the container to retain the syringe therein, evacuating the sealed container, and filling the container with the same gas as in the syringe using the valve.

In accordance with still yet another aspect of the present invention, a method of preparing a gas-filled syringe is provided which comprises the step of filling a container with a predetermined volume of a selected gas via an opening therein. The container is formed from a high gas barrier material to prevent gas from escaping from the container once the opening is sealed. The method further comprises the step of puncturing the container with the syringe needle and drawing the gas into the syringe by retracting the syringe plunger.

A further aspect of the invention is basically attained by providing a method of introducing a gas into the eye during eye surgery, the method comprising the steps of providing a clean and sterile prefilled syringe containing a unit dose of a pharmaceutically acceptable gas and being substantially free of air and oxygen, the syringe having a syringe barrel, a gas delivery outlet, and a plunger. The syringe is completely enclosed in a substantially gas impermeable container, and the container has an internal volume surrounding the syringe filled with the pharmaceutically acceptable gas at a pressure at least substantially equal to atmospheric pressure. The syringe is removed from the container, and the gas delivery outlet is introduced into the eye of a patient and the gas is introduced into the eye.

BRIEF DESCRIPTION OF THE DRAWINGS

These and other features and advantages of the present invention will be more readily apprehended from the following detailed description when read in connection with the appended drawings, in which:

FIG. 1 is an isometric view of a container and cover constructed in accordance with an embodiment of the present invention for containing a gas and enclosing a syringe filled with gas;

FIG. 2 is a side cross-sectional view of the container and cover depicted in FIG. 1 showing the syringe contained therein;

DETAILED DESCRIPTION OF THE PREFERRED EMBODIMENTS

Figures 1, 2:
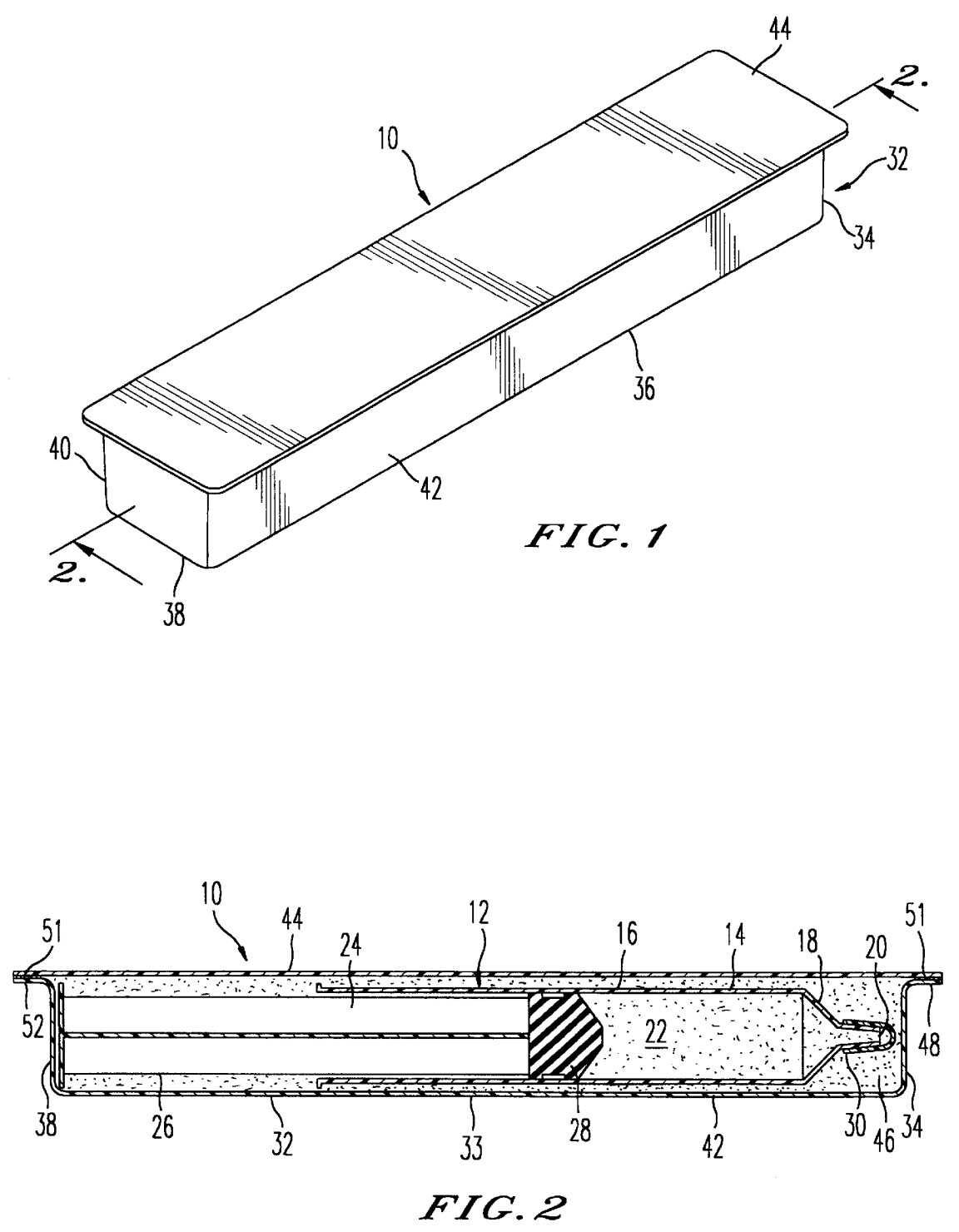
Figure 3:
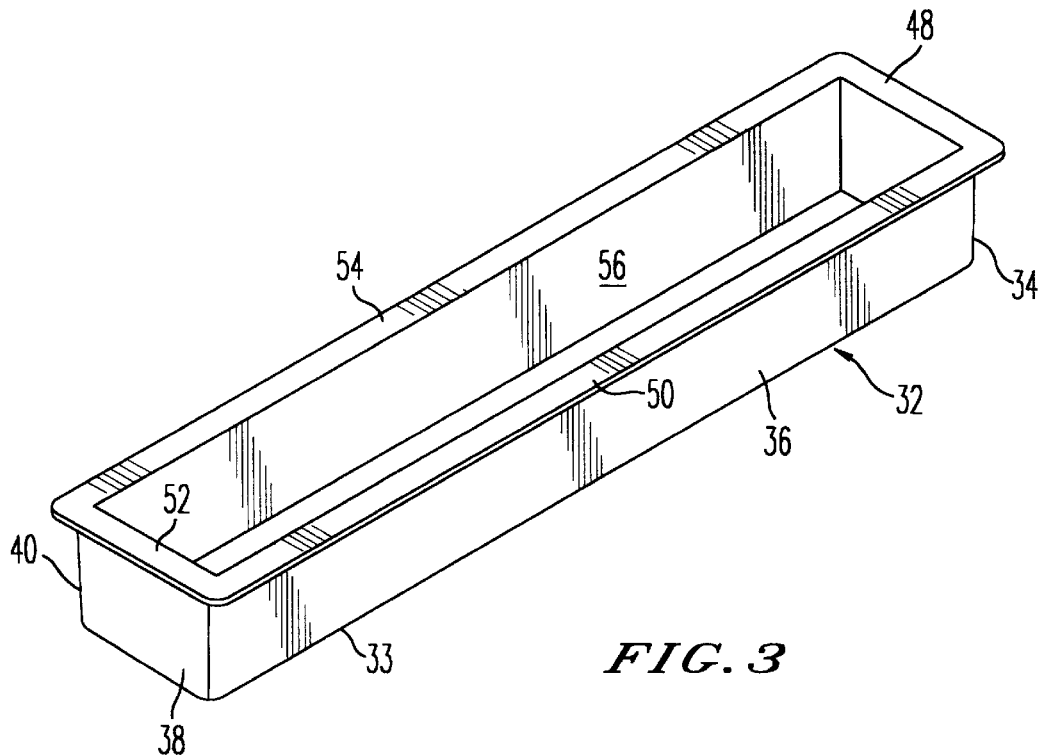
FIG. 3 is a top view of the container depicted in FIG. 1 without the cover or syringe.

With reference to FIG. 1, a container 10 for enclosing a gas syringe 12 is shown in accordance with an embodiment of the present invention. Before describing the container 10, an exemplary syringe 12, as shown in FIG. 2, will be described. It is to be understood that other types of gas-filled syringes can be used in accordance with the present invention. The exemplary gas syringe 12 comprises a tubular housing 14 defining a syringe barrel having longitudinally cylindrical section 16, a frustoconical section 18 and a gas delivery outlet forming a gas dispensing tip 20 which are all preferably formed as an integral, unitary member. The tubular housing can be formed from a material with a high degree of gas impermeability such as glass. The tubular housing, however, can be a gas permeable material such as plastic since the container 10 of the present invention is designed to prevent dilution and contamination of the syringe contents, as will be described in further detail below.

With continued reference to FIG. 2, the interior circumference of the tubular housing 14 defines a cavity 22 which can be filled with a selected gas in a conventional manner. The gas is retained within the cavity 22 by a plunger 24. The end of the plunger 24 that is proximal with respect to the frustoconical section 18 of the housing 14 can be provided with a stopper 28 which is dimensioned to slidably engage the inner circumference of the cylindrical section 16 of the tubular housing 14 to controllably change the level of gas pressurization within the cavity 22. The tip 20 can be fitted with a removable cap 30. The syringe, however, can be open at the tip 20, or have a cannula or needle or other delivery device on the tip 20, or have an integral needle or tube molded on the front of the syringe. In any case, the container 10 is designed to prevent the gas in the syringe 12 from being diluted or contaminated by atmospheric air or contaminants regardless of whether the cavity 22 is completely sealed.

With reference to FIGS. 1, 2 and 3, the container 10 comprises a bottom portion 32 and a top portion 44. In accordance with an embodiment of the present invention, the bottom portion 32 is preferably molded or otherwise formed to create a trough or open container dimensioned to at least accommodate the syringe 10 having its plunger 24 at least partially withdrawn from the cavity 22 of the housing 14. For example, the bottom portion 32 can comprise a bottom wall 38 and four side walls 34, 36, 38 and 40 which preferably form a unitary, integral member defining a cavity 46 in which the syringe is placed. The tops of the side walls 34, 36, 38 and 40 are each provided with a flange 48, 50, 52 and 54. The top portion 44 is dimensioned to cover the opening 56 of the bottom portion 32 of the container 10, as well as engage each flange 48, 50, 52 and 54. The top portion 44 and the bottom portion therefore can be sealed together using, for example, an adhesive 51 on the flanges 48, 50, 52 and 54. Alternatively, the material from which the top portion 44 and the bottom portion 32 are formed can be fused together via heat sealing, as indicated at 53 in FIG. 5. In either case, the sealed joint formed at the flanges 48, 50, 52 and 54 satisfies the gas barrier criteria sufficient to maintain the purity of the contents (i.e., gas) in the container 10 and syringe 12, if a syringe is placed in the container 10.

Figure 4:
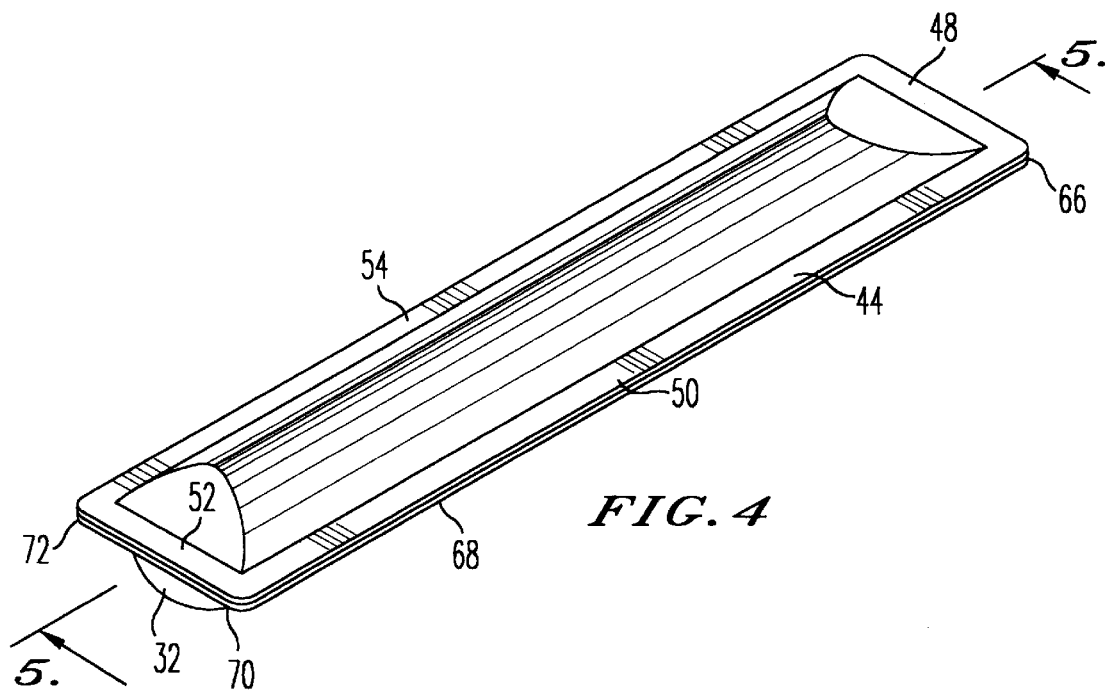
FIG. 4 is an isometric view of a container constructed in accordance with an embodiment of the present invention for containing a gas and enclosing a syringe filled with gas.
Figure 5:
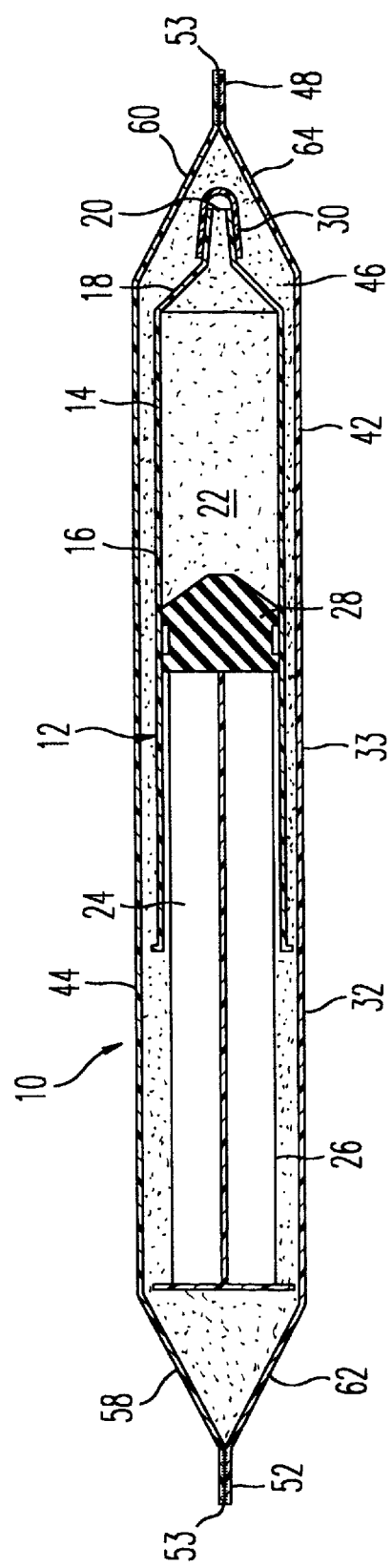
FIG. 5 is a side cross-sectional view of the container depicted in FIG. 4 showing the syringe contained therein.
Figure 6:
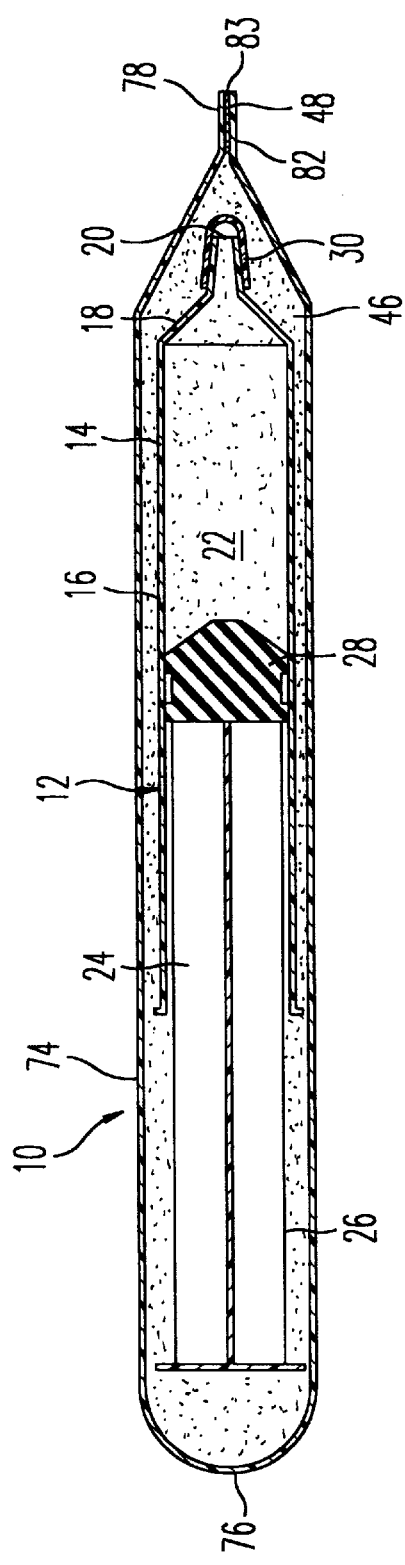
FIG. 6 is a side cross-sectional view of a container constructed in accordance with another embodiment of the present invention for containing a gas.

Although the bottom portion 32 of the container is shown as rectangular in shape and having a rectangular recess or trough, a variety of shapes can be used. For example, the bottom portion 32 of the container can be formed into a more complicated shape than a rectangle to approximately conform to the shape of its contents (e.g., a syringe 12). In addition, the top portion 44 need not be planar. For example, as shown in FIGS. 4 and 5, the top portion 44 and the bottom portion 32 of the container 10 can both be nonplanar and configured to form the cavity 46 when adhered together. Further, the top portion 44 and the bottom portion 32 of the container 10 can be configured to have a curvilinear cross-section (FIG. 4) with tapered ends 58 and 60, and 62 and 64, respectively (FIG. 5). The ends are adhered together along the flanges 48, 50, 52 and 54 of the bottom portion and corresponding flanges 66, 68, 70 and 72 of the top portion 44 of the container 10. Alternatively, the top portion 44 and bottom portion 32 of the container 10 can be formed as a unitary and integral piece of high gas barrier material designated as 74 in FIG. 6 which is folded on one side 76 thereof. The two, free ends 78 and 82 are then sealed with an adhesive layer 83 or by heat sealing depending on the material used to form the container 10. The container 10 and the syringe 12 are preferably clean and sterile according to conventional standards for surgical equipment.

In accordance with an embodiment of the invention, the container 10 is preferably made of a high gas barrier material such as a metallized polymer laminate which can be sealed to retain a selected gas inside the container. The container 10 is preferably made from a material that is substantially impermeable to oxygen and other atmospheric gases and substantially impermeable to sterilizing gases such as ethylene oxide. The syringe 12 is filled in a conventional manner with a unit dose of the selected gas (e.g., sulfur hexafluoride or nitric oxide). The syringe 12 is then placed within the bottom portion 32 of the container 10 with the plunger 24 at least partially withdrawn from the cavity 22. The container 10 is then filled with preferably the same gas as the syringe 12 and sealed using the top portion 44 (e.g., by applying an adhesive or heat sealing along the flanges 48, 50, 52 and 54 of the bottom portion 32 to adhere to the edges of the top portion 44).

Alternatively, the container 10 can be made from a sheet 74 of high gas barrier material that is folded. A gas-filled syringe can be placed between the two free ends 78 and 82 of the sheet 74. The space between the free ends is then filled with the same gas and sealed to enclose the gas and gas-filled syringe. Thus, the sealed container 10 provides a sufficient gas barrier to prevent the gaseous content of the container, and therefore the syringe, from leaking or diffusing outside the container, and to prevent atmospheric gaseous contaminants from diffusing into the container and the syringe. Further, the use of the same gas inside the container as well as inside the syringe facilitates the maintenance of the selected gas within the syringe since any gas exchange occurring through the walls of the syringe does not dilute the unit gas dose therein. The gas within the container is generally maintained at a pressure to inhibit diffusion of oxygen and other atmospheric gases into the container, thereby inhibiting dilution of the gas. In embodiments, the gas in the container is at a pressure greater than atmospheric pressure.

In preferred embodiments, the gas is a pharmaceutically acceptable gas as known in the medical field which is substantially in the absence of oxygen, air and other atmospheric gas contaminants. Examples of suitable gases include nitric oxide, nitric oxide releasing compounds, carbon dioxide, perfluoropropane, perfluorobutane, perfluoroethane, helium and sulfur hexafluoride. Generally, the gas has a purity level of at least 70% by volume and preferably at least about 93% to about 98% by volume. In embodiments, the gas is at least about 97% pure. In preferred embodiments, the syringe and the container are filled with the same gas having substantially the same purity to inhibit diffusion of gases between the gas in the cavity of the container and cavity of the syringe barrel.

As stated previously, the high gas barrier material for the container 10 prevents diffusion of gas molecules from the atmosphere through the container walls and therefore dilution or contamination of the unit gas dose within the syringe 12. The shelf life of the unit gas dose is determined by the rate at which gaseous contaminants such as oxygen molecules from the surrounding atmosphere diffuse into the container 10, or the rate at which the selected gas inside the container 10 diffuses out. The following formula can be used to calculate the maximum allowable gas transmission rate $GTR_{MAX}$ for the container material:

$$GTR_{MAX} = V \times \frac{(1-P)}{A \times S}$$

where V is the volume of the container 10, P is the minimum acceptable purity of the unit gas dose in the syringe 12, A is the surface area of the container 10, and S is the desired shelf life of the unit gas dose in syringe 12.

By way of an example, a unit dose of sulfur hexafluoride of at least ninety-five percent (i.e., P=95%) purity is desired. The syringe 12 is packaged in a container 10 having a volume V of 20 cubic inches and a surface area A of 64 square inches. A one year shelf life is desired. The maximum allowable gas transmission rate $GTR_{MAX}$ for the container 10 material is therefore 0.0156 cubic inches per square inches per year (or 0.07 cc per 100 square inches per 24 hours). A purity level of 95% in the example above was chosen for illustrative purposes only. The minimum acceptable purity level of gas can vary, depending on the type of gas used and the application for its use. Embodiments providing higher or lower priority levels are covered under the scope of the present invention.

Suitable materials for the container 10 can include, but are not limited to, metal foils such as aluminized foil laminates. Other examples of container 10 material include laminates having one or more metallized layers of nylon, oriented polypropylene (OPP), polyethylene (PE), ethylene vinyl alcohol (EVOH), polyethylene terephthalate (PET), low density polyethylene (LDPE), medium density polyethylene (MDPE), and/or cellophane. A lacquer coating can also be used to create a cold seal.

The container can be made from a suitable gas impermeable laminate having a sufficiently low permeability to inhibit or substantially prevent the diffusion of air or oxygen from the atmosphere into the container and to inhibit diffusion of the medical gas in the syringe and container from diffusing outward. The container formed from gas impermeable films are also impermeable to ethylene oxide so that other forms of sterilization must be used. Gamma radiation at conventional sterilizing dosages can be used to effectively sterilize the syringe and contents.

Suitable laminated films include materials sold under the trademark ACLAR by Ted Pella, Inc. which is a transparent fluorinated-chlorinated thermoplastic. Other materials include silica coated polyester films sold under the tradename Clearfoil by Rollprint Packaging Products, Inc. of Addison, Ill., a polypropylene, polyethylene, polyethylene vinyl alcohol and Bynel laminate sold under the trademark EVALIGHT by DuPont. Preferably, the container 10 is sufficiently impermeable to oxygen and other atmospheric gases to provide a shelf life of the syringe of about one year where the gas purity in the syringe is substantially unchanged. In further embodiments, the packaged syringe has a shelf life of at least about 6 months to about 5 years, and typically about 1–2 years.

Some of the gases used in surgery have large molecules which cannot pass through polymeric or metallic films as readily as oxygen. Oxygen and other gaseous contaminants cannot dilute the unit gas dose in the syringe 12 unless one of two conditions exists. First, if the container 10 material allows some of the selected gas in the container to diffuse out into the atmosphere, then the volume of gas lost in the container 10 is replaced with other gas constituents from the atmosphere. Second, if the pressure in the container 10 is less than atmospheric pressure outside the container, then the gaseous contaminants may diffuse into the container regardless of whether any interior container gas diffuses out. If the pressure in the container 10 is essentially maintained above the atmospheric pressure, then the container material can be chosen on the basis of the transmission rate of the gas in the container. In cases where the selected gas is characterized by large molecules, materials providing considerably lower gas barriers can be used as compared with materials providing barriers to gases with relatively small molecules. If the pressure in the container is not maintained above atmospheric pressure, then the highest relevant gas transmission rate, which is typically the gas transmission rate of oxygen in the surrounding atmosphere, is preferably used as the basis for selecting a container material.

A controlled atmosphere of a selected gas inside the container 10 can be achieved in a number of ways. For example, a form/fill/seal machine can be used. The form/fill/seal machine provides an evacuated assembly area therein which is filled with the selected gas. The web(s) of a high gas barrier material selected to construct one or more containers 10 is feed into the area. One part of the container can be formed, for example, with a recess or trough of sufficient size to accommodate a pre-filled gas syringe therein. The container construction is then completed by enclosing the syringe within the container using, for example, another piece of the web to cover the recess. The other piece of the web can be sealed against the first part of the web using an adhesive or heat sealing. The controlled gaseous assembly area, therefore, ensures that the container is filled with the same gas as the syringe to avoid the aforementioned problem of dilution caused by gas contaminants mixing with the contents of the syringe inside the container 10.

Alternatively, a controlled atmosphere of a selected gas inside the container 10 can be achieved by providing the container with a valve which permits evacuation of a sealed container having a pre-filled gas syringe enclosed therein and subsequent filling of the container with the selected gas. Further, the container 10 need not be provided with a syringe 12 at all. In accordance with an embodiment of the present invention, the container 10 can be filled with a selected gas (e.g., using a form/fill/seal machine that does not insert a syringe prior to sealing, or by evacuation, ejection with a selected gas and sealing). The container 10 containing the selected gas can then be drawn into an empty syringe by puncturing the container 10 with a needle and drawing the gas into the syringe cavity 22 with the plunger 24. Alternatively, a syringe can be constructed with a sufficiently gas impermeable tubular housing 14, stopper 28 and cap 30 combination to obviate the need for a container 10. The syringe can therefore be pre-filled with a selected gas prior to use and prevent contamination of the gas therein until the cap 30 is removed.

Figure 7:
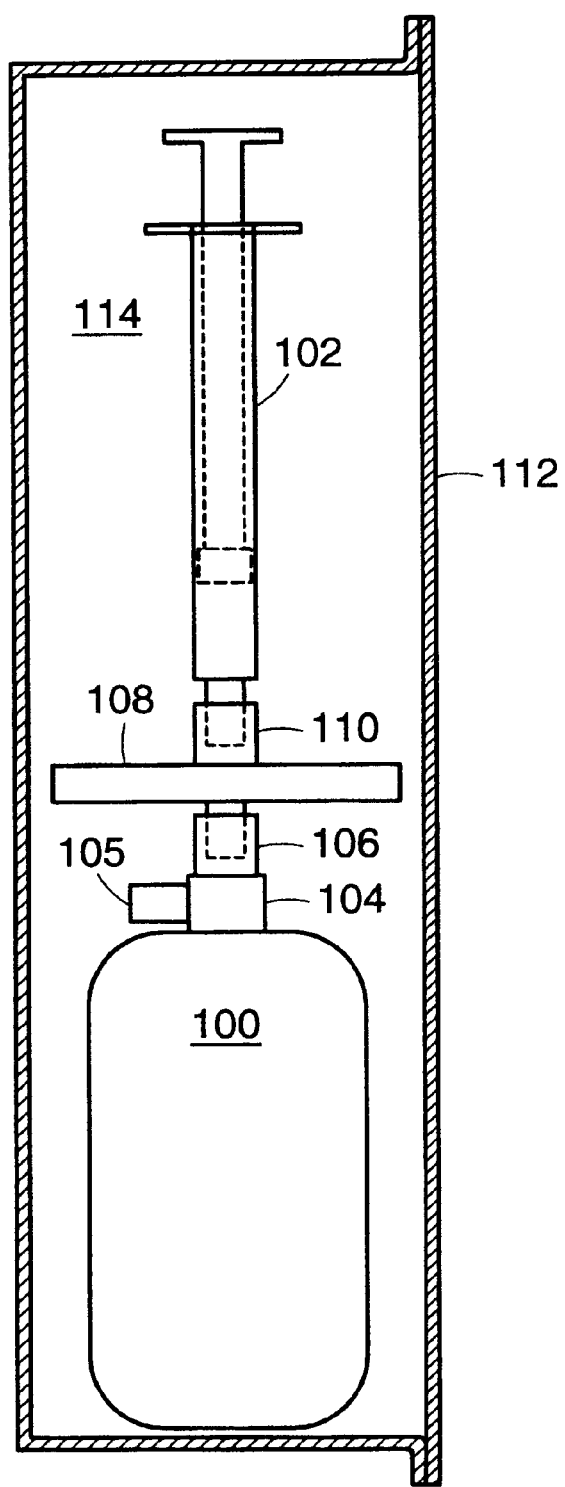
FIG. 7 is a top view of a syringe and canister in a container in a further embodiment of the invention.

In a further embodiment shown in FIG. 7, a pressurized gas canister 100 is coupled to a syringe 102 for filling the syringe 102 with a medical gas. The canister can be made of metal, plastic, glass or other suitable materials capable of maintaining the gas under sufficient pressure to fill the syringe. The canister 100 includes a manually operated valve 104 having an actuating button 105. The valve 104 has a coupling member 106, such as a threaded coupling, for connecting to a filter housing 108. The filter housing 108 is typically a HEPA filter as known in the art to remove particulates and other impurities. An outlet coupling 110 is provided in the filter housing 108 for connecting to the syringe 102. The syringe 102 in the embodiment illustrated has a luer lock type fitting for coupling to the filter. In further embodiments, the syringe can have a needle for piercing a septum or membrane on the outlet coupling 110 of the filter housing 108. Alternatively, the syringe can have a tapered tip for attaching to the coupling 110 and for receiving a needle or other delivery outlet or device. In use, the button 105 is depressed to release the gas from the canister to fill the syringe. Typically, the canister containers a sufficient amount of gas to flush the syringe to remove any contaminants which may be present. In embodiments of the invention, the syringe and canister are enclosed in a container 112 having a cavity 114 containing the same gas as the gas in the canister. Preferably, the gas in the canister and the container 112 is substantially pure in the absence of oxygen and other atmospheric gases. The container 112 is made from the same materials as in the previous embodiments.

The container 10, whether it is provided with a syringe 12 therein or not, is preferably sterilized so it can be used in surgery, for example. A number of methods for sterilization can be used. The container 10 can be sterilized, for example, as it is being formed inside a form/fill/seal machine. The syringe can be sterilized before it is inserted into a sterile chamber in the form/fill/seal machine, or the syringe 12 and new formed container 10 can both be sterilized as they are assembled together. A container 10 containing only gas and no syringe can be sterilized inside a form/fill/seal machine or be sterilized after it is assembled and before it is filled with gas if an atmosphere-controlled assembly and fill area is not available.

In accordance with the present invention, a pre-filled package containing a unit dose of medical gas and method of making same is provided. The pre-filled package can be a package, a package containing a syringe or a syringe having a gas impermeable chamber. The pre-filled package prevents contamination of the gas therein for use in a number of applications, such as injection of a gas bubble into a patient's eye for treating a retinal tear, or injection of carbon dioxide into a blood vessel to displace blood and allow an improved field of view during percutaneous angioscopy. The material with which the package is made is selected to maintain a desired purity level of gas within the package. Further, the aforementioned problems associated with dispensing expensive gases from a tank in preparation for a medical procedure are avoided.

In the method of the invention, the syringe is removed from the container and the delivery device, such as a needle, is introduced in the desired location in the body of the patient being treated. The syringe plunger is then depressed to inject a unit dose of the gas into the patient. The gas can be injected into a vein or vessel, the ocular cavity of an eye during eye surgery, the spinal column, and the like, as known in the medical and surgical field. When performing surgery in the eye, such as retinal surgery, the injected gas is an ophthalmologically acceptable gas.

While certain advantageous embodiments have been chosen to illuminate the invention, it will be understood by those skilled in the art that various changes and modifications can be made herein without departing from the scope of the invention as defined in the appended claims.

What is claimed is:

1. A gas syringe for injecting a gas into the body of an animal, said syringe comprising:

a prefilled gas syringe containing a unit dose of a pharmaceutically acceptable gas, said gas being substantially in the absence of air, said syringe including a syringe barrel with a gas delivery outlet, and a plunger slidably received in said syringe barrel for expelling said unit dose of said gas through said delivery outlet; and a container enclosing said gas syringe to prevent contact of said gas syringe with air and contaminants external to said container, said container having an internal volume containing said gas substantially in the absence of air, said container being made of a substantially gas impermeable material and said container having an internal pressure to inhibit diffusion of air and contaminants into said container.

2. The gas syringe of claim 1, wherein said container has an internal surface area defining said unit dose of said gas, and said gas in said syringe has a purity of at least about 95%, said gas having a shelf life of at least one year, said gas barrier material to have a maximum allowable gas transmission rate determined using $V \times (1-p)/(A \times S)$, wherein V is a volume of said container, p is the purity of said gas, A is the internal surface area of said container, and S is said shelf life.

3. The gas syringe of claim 1, wherein said gas is selected from the group consisting of nitric oxide, nitric oxide-releasing compounds, carbon dioxide, perfluoropropane, perfluorobutane, perfluoroethane, helium, and sulfur hexafluoride.

4. The gas syringe of claim 1, wherein said gas barrier material is selected from the group consisting of a metal foil, an aluminized foil laminate, and a laminate having at least one metallized layer of at least one layer of nylon, polypropylene, ethylene vinyl alcohol, polyethylene terephthalate, low density polyethylene, medium density polyethylene or cellophane.

5. The syringe of claim 1, wherein said gas delivery outlet is a needle.

6. The syringe of claim 1, wherein said gas is substantially free of oxygen and is at least about 93% by volume pure.

7. The syringe of claim 1, wherein said gas in said container is at a pressure above atmospheric pressure.

8. The syringe of claim 1, wherein said container is made from a metal foil laminate.

9. The syringe of claim 1, further comprising a canister containing said pressurized gas, said canister having an outlet removably coupled to said delivery outlet for supplying said gas to said syringe.

10. A method of introducing a gas into the body of an animal comprising the steps of:

provid ing a clean and sterile packaged, prefilled syringe having a syringe barrel, delivery outlet and plunger, said syringe containing a unit dose of a pharmaceutically acceptable gas, said gas being substantially free of air, wherein said prefilled syringe is enclosed in a container, said container being formed from a material substantially impermeable to air and said pharmaceutically acceptable gas and having an internal volume surrounding said syringe and being filled with said gas at a pressure at least substantially equal to atmospheric pressure, removing said syringe from said container, and introducing said delivery outlet into an animal and injecting said gas into said animal.

11. The method of claim 10, wherein said delivery outlet is a needle or cannula.

12. The method of claim 10, wherein said pharmaceutically acceptable gas has a purity of at least about 70% by volume.

13. The method of claim 10, wherein said pharmaceutically acceptable gas has a purity of about 93% to 98% by volume.

14. The method of claim 10, wherein said container has a gas permeability to provide a shelf life of said gas in said syringe of at least one year.

15. The method of claim 10, wherein said pharmaceutically acceptable gas is selected from the group consisting of nitric oxide, nitric oxide-releasing compounds, carbon dioxide, perfluoropropane, perfluoroethane, perfluorobutane, helium and sulfur hexafluoride.

16. The method of claim 10, wherein said container is made from a laminate material having at least one metal foil layer and a layer selected from the group consisting of nylon, polypropylene, polyethylene, ethylene vinyl alcohol, polyethylene terephthalate and cellophane.

17. The method of claim 10, wherein said container is formed from a material having a sufficiently low gas permeability whereby the purity of said gas in said container is substantially unchanged after about one year.

18. The method of claim 10, wherein said container is made from a substantially oxygen impermeable material.

19. The method of claim 10, wherein said gas in said container is at a pressure above atmospheric.

20. A method of introducing a gas into the eye during eye surgery, said method comprising the steps of providing a clean and sterile prefilled syringe containing a unit dose of a pharmaceutically acceptable gas and being substantially free of air and oxygen, said syringe having a syringe barrel, a gas delivery outlet, and a plunger, said syringe being completely enclosed in a substantially gas impermeable container, said container having an internal volume surrounding said syringe and being filled with said pharmaceutically acceptable gas at a pressure at least substantially equal to atmospheric pressure, removing said syringe from said container, and introducing said gas delivery outlet of said syringe into the eye of a patient and introducing said gas into the eye.

21. The method of claim 20, wherein said pharmaceutically acceptable gas has a purity of at least about 93% to 98% by volume.

22. The method of claim 20, wherein said pharmaceutically acceptable gas is selected from the group consisting of nitric oxide, nitric oxide-releasing compounds, carbon dioxide, perfluoropropane, perfluoroethane, perfluorobutane, helium and sulfur hexafluoride.

* * * * *